United States Patent

Kakimoto et al.

[11] Patent Number: 6,146,638
[45] Date of Patent: Nov. 14, 2000

[54] FERMENTED GARLIC COMPOSITION

[75] Inventors: Masanori Kakimoto; Ayumi Suzuki; Isao Nishimoto; Sumihiro Shiraishi; Yoichi Itakura, all of Hiroshima, Japan

[73] Assignee: Wakunaga Pharmaceutical Co., Ltd., Osaka, Japan

[21] Appl. No.: 09/319,690

[22] PCT Filed: Nov. 27, 1997

[86] PCT No.: PCT/JP97/04327

§ 371 Date: Jun. 10, 1999

§ 102(e) Date: Jun. 10, 1999

[87] PCT Pub. No.: WO98/25481

PCT Pub. Date: Jun. 18, 1998

[30] Foreign Application Priority Data

Dec. 10, 1996 [JP] Japan ................................. 8-329727

[51] Int. Cl.[7] ........................ A01N 65/00; A61K 47/00; A61K 9/14

[52] U.S. Cl. ........................ 424/195.1; 424/439; 424/489

[58] Field of Search ................... 424/195.11, 489, 424/439, 464

[56] References Cited

U.S. PATENT DOCUMENTS 4,820,529  4/1989  Uchida et al. ........................ 426/7

FOREIGN PATENT DOCUMENTS 38-14392  8/1963  Japan .
7-46966   2/1995  Japan .

Primary Examiner—Thurman K. Page
Assistant Examiner—Susan Tran
Attorney, Agent, or Firm—Oblon, Spivak, McClelland, Maier & Neustadt, P.C.

[57] ABSTRACT

The present invention relates to a composition prepared by fermenting enzymatically-deactivated garlic with Aspergillus and/or Monascus, to a process for preparing the same, and also to foods and drugs containing the same. The composition is free from any unpleasant odor and is useful as a prophylactic or therapeutic agent for diabetes, hepatic diseases, cancer, immunopathy, hyperlipemia, and the like.

15 Claims, 5 Drawing Sheets

FERMENTED GARLIC COMPOSITION

TECHNICAL FIELD

The present invention relates to a fermented garlic composition, a process for producing the same, and a food and a drug containing the same.

BACKGROUND ART

Since ancient times, garlic has been consumed as a seasoning or spice. In recent years, garlic has been found to contain a variety of physiologically active components, and therefore, garlic is widely used as a health food and a drug.

However, garlic contains an odor precursor which is easily converted to an odorous component such as allicin or diallyl disulfide, to thereby impart an unfavorable taste which many people dislike. Therefore, there have been developed methods for producing odorless garlic through heat treatment, as disclosed in, e.g., Japanese Patent Application Laid-Open (kokai) Nos. 59-216565 and 4-12604. However, there still remain problems, such as generation of a garlic odor after eating.

Meanwhile, standardizing a method for processing garlic is important in view that the components or physiological activity of garlic depends on differences in processing conditions (Emiko MOTIZUKI: *FOODS & FOOD INGREDIENTS JOURNAL OF JAPAN* 164, 36–45, 1995).

Apart from garlic, there has conventionally been employed a method of fermentation making use of Aspergillus and/or Monascus for producing miso, soy sauce, sake, etc. The safety of Aspergillus and that of Monascus have already been substantiated on the basis of long-term dietary experience, and a variety of physiological effects provided by Aspergillus and/or Monascus are reported (e.g., anti-oxidation activity (Naohiko YAMAGUCHI: *Nihon Shokuhin Kogyo Gakkaishi* 26, 71–75, 1979) and inhibitory activity against angiotensin I converting enzyme (Takeyori TERANAKA, et al.: *Nihon Nogeikagakukaishi* 69, 1163–1169, 1995) provided by Aspergillus; or activity for reduction of cholesterol, antihypertension, etc. provided by Monascus).

Thus, the present inventors considered that a composition having no garlic odor and being useful as a drug or a food could be produced by fermenting garlic by use of Aspergillus and/or Monascus. According to the investigation thereon, garlic could not be fermented by use of Aspergillus and/or Monascus, since garlic per se exhibits antibacterial activity. Although Japanese Patent Application Laid-Open (kokai) No. 48-52995 discloses a process whereby a small amount of garlic is added during a production step of wine, and Japanese Patent Application Laid-Open (kokai) No. 53-26361 discloses a process whereby fermentation is induced by addition of a large amount of sugar to a small amount of garlic, no process of fermentation employing garlic as a predominant source has been reported.

Accordingly, an object of the present invention is to provide a composition useful as a drug or food and produced by fermenting garlic by use of Aspergillus and/or Monascus to thereby remove a characteristic garlic odor.

DISCLOSURE OF THE INVENTION

In view of the foregoing, the present inventors have conducted earnest studies and have found that enzymatic deactivation of garlic performed in advance enables fermentation thereof by use of Aspergillus and/or Monascus without addition of a nutrient such as glucose or starch. Moreover, the present inventors have also found that the obtained fermented composition has no garlic odor and has anti-oxidative activity about 100 times that of intact garlic, as well as actions such as anti-diabetes activity, activity for protection from liver disease, anti-cancer activity, immunity-enhancing activity, and cholesterol-reducing activity, to thereby be useful for treatment and prevention of diabetes, hepatic diseases, cancer, immunopathy, hyperlipemia, and the like. The present invention has been accomplished based on this finding.

Accordingly, the present invention provides a composition prepared by fermenting enzymatically-deactivated garlic by use of Aspergillus and/or Monascus, as well as a food and a drug containing the same.

The present invention also provides a pharmaceutical composition comprising a composition prepared by fermenting enzymatically-deactivated garlic by use of Aspergillus and/or Monascus, and a pharmaceutically acceptable carrier.

The present invention also provides use, as a drug, of a composition prepared by fermenting enzymatically-deactivated garlic by use of Aspergillus and/or Monascus.

The present invention also provides a method for treating a disease selected from among diabetes, a hepatic disease, cancer, immunopathy, and hyperlipemia by administering an effective amount of a composition prepared by fermenting enzymatically-deactivated garlic by use of Aspergillus and/or Monascus.

The present invention further provides a process for producing a fermented garlic composition by fermenting enzymatically-deactivated garlic by use of Aspergillus and/or Monascus.

BEST MODE FOR CARRYING OUT THE INVENTION

Figure 1:
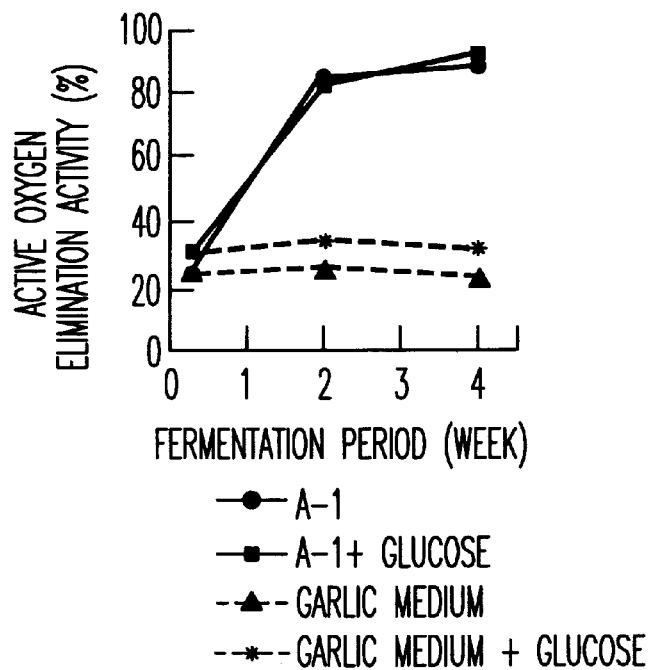
FIG. 1 is a graph showing active oxygen elimination activity.

In the present invention, "garlic" refers to *Allium sativum* L., which belongs to Liliaceae Allium.

A bulb portion of garlic is particularly preferable for fermentation, and an enzymatically-deactivated garlic bulb may be subjected to fermentation as is or after being sliced into an arbitrary dimension or crushed to produce juice thereof. Furthermore, beans and/or cereals such as rice, soybeans, wheat, and adlay (coix lacrima-jobi) may be added in accordance with needs.

In the production of the fermented garlic composition according to the present invention, first, garlic is enzymatically deactivated. The enzymatic deactivation of garlic may be carried out with heat, microwave radiation, high pressure, an enzyme, acid, or alcohol. Of these, heat treatment is preferred, in view of simplicity. The treatment is preferably carried out at 50–200° C. for 1–60 minutes, particularly preferably at 90–121° C. for 10–30 minutes.

The enzymatically-deactivated garlic is fermented by use of one or more strains selected from the genus Aspergillus, such as *Aspergillus oryzae, Aspergillus sojae, Aspergillus kawachi*, or *Aspergillus awamori*, or the genus Monascus, such as *Monascus pilosus, Monascus anka, Monascus paxii, Monascus pubigerus, Monascus purpures, Monascus ruber, Monascus vitreus*, or *Monascus major*, to thereby obtain a target fermented garlic composition.

Specifically, the fermented garlic composition may be prepared through the following steps.

1) Preparation of a Garlic Culture Medium/Garlic-Containing Culture Medium

Garlic is washed with water and boiled with an equal volume of water for 20–30 minutes. The boiled garlic is subjected to a process such as mincing or crushing in accordance with needs. (When crushing is employed, obtained juice may be used exclusively.) Furthermore, beans and/or cereals such as rice, soybeans, wheat, and adlay may be added as nutrients to the processed garlic, or the processed garlic may be chaptalized, and the resultant material is sterilized (121° C., 20 minutes) in an apparatus such as an autoclave. The amount of added beans and/or cereals or that of chaptalization is controlled so as not to exceed 90 wt. % based on the entirety (hereinafter referred to simply as %).

2) Preculture of a Strain for Fermentation

Examples of the strains which are preferably used for fermentation include one or more strains selected from the genus Aspergillus, such as *Aspergillus oryzae, Aspergillus sojae, Aspergillus kawachi*, or *Aspergillus awamori*, or the genus Monascus such as *M. pilosus, M. anka, M. paxii, M. pubigerus, M. purpures, M. ruber, M. vitreus*, or *M. major*.

The strains are subcultured by use of a 2% yeast extract-added potato dextrose agar medium. The subcultured strains are inoculated to a subsequent culture medium, and cultured at 10–50° C. for 2–14 days, preferably at 20–40° C. for 2–4 days.

Examples of the media for preculturing include Sabouraud's agar medium (peptone 1%, glucose 4%), potato dextrose agar medium (tea of potato (200 g/l) glucose 2%), glycerin medium (glycerin 7%, glucose 3%, Soybean meal 3%, peptone 0.3%, magnesium sulfate 0.1%, sodium chloride 0.2%) and any medium for culturing Eumycetes. Edible material is preferably incorporated into culture media.

3) Fermentation of Garlic

The preculture liquid prepared in step 2 is added in an amount of 0.1–50%, preferably 0.5–10%, to the garlic medium prepared in step 1. Subsequently, culturing is carried out at 10–50° C. for 7–60 days, more preferably at 20–40° C. for 7–35 days in the case of Aspergillus or for 14–42 days in the case of Monascus, through stationary culture or shaking culture, to thereby prepare a fermented garlic composition. Alternatively, stationary culture may be carried out through monoculture by reducing the water content of a culture medium to 40–60%.

4) Processing of a Fermented Garlic Composition

Upon completion of fermentation in step 3, the fermented product is sterilized with heat. The sterilized product may be used as is or after isolation from the culture filtrate. Alternatively, an active component may be taken up from the sterilized product and submitted for use.

The thus-obtained composition according to the present invention may be processed into food through a customary method or, along with a pharmaceutically acceptable carrier, into a drug having any of a variety of forms.

In order to prepare an oral solid formulation, an excipient and optional additives such as a binder, a disintegrator, a lubricant, a colorant, and a flavoring agent are added to a fermented garlic composition, and the mixture is processed into any of a variety of formulations such as tablets, coated tablets, granules, powder, and capsules through a customary method. Additives generally used in the art may serve as such additives. Examples of excipients include lactose, sucrose, sodium chloride, glucose, starch, calcium carbonate, kaolin, microcrystalline cellulose, and silicic acid. Examples of binders include water, ethanol, propanol, simple syrup, glucose liquid, starch liquid, gelatin liquid, carboxymethyl cellulose, hydroxypropyl cellulose, hydroxypropyl starch, methyl cellulose, ethyl cellulose, shellac, calcium phosphate, and polyvinylpyrrolidone. Examples of disintegrators include anhydrous starch, carmellose-Ca, sodium alginate, agar powder, sodium hydrogencarbonate, calcium carbonate, sodium laurylsulfate, stearic acid monoglyceride, and lactose. Examples of lubricants include purified talc, stearate salts, borax, and polyethylene glycol. Examples of flavoring agents include sucrose, bitter orange peel, citric acid, and tartaric acid.

In order to prepare an oral liquid formulation, additives such as a taste improver, a buffer, a stabilizer, a flavoring agent, etc. are added to a fermented garlic composition, and the mixture is processed through a customary method into any of a variety of formulations such as oral medicine liquid, a syrup, or an elixir. In this case, any one the above-listed flavoring agents may be employed. Examples of buffers include sodium citrate, and examples of stabilizers include tragacanth, acacia, and gelatin.

The food or drug according to the present invention can be used for treatment and prevention of diabetes, hepatic diseases, cancer, immunopathy, hyperlipemia, and the like.

The dose and manner of administration may be suitably determined in accordance with the patient's age, body weight, and symptoms. The daily dose of the composition according to the present invention for an adult is preferably 0.5–2 g, administered at a single time or in a divided manner.

The composition according to the present invention is generally of low toxicity, since the composition predominantly comprises garlic and Aspergillus or Monascus, which are generally provided for foods. When the composition according to the present invention was mixed with feed in an amount of 3% and fed to juvenile rats for three weeks, no abnormalities in growth or general behavior were observed. Thus, the composition was confirmed to be a highly safe substance.

The fermented garlic composition according to the present invention has strong anti-oxidative activity and exhibits actions such as carcinostatic activity; immunity-enhancing activity, e.g., to NK activity; activity for protection from an acetoaminophene liver disorder; activity for protection with respect to an alloxan diabetes model; anti-diabetes activity by enhancing glucose tolerance; and cholesterol-reducing activity. Thus, the composition is remarkably useful for treatment and prevention of adult diseases which are prevalent in present-day society.

In addition, the composition according to the present invention has high safety and almost no garlic odor (no odor is generated in the mouth, in contrast with the case of odorless garlic obtained by deactivating alliinase), to thereby serve widely as an ingredient for health foods and pharmaceuticals.

EXAMPLES

The present invention will next be described in detail by way of examples. However, the present invention is not limited only to these examples. Strains of the genus Aspergillus and Monascus used in the Examples are shown in Table 1.

TABLE 1

| Abbreviation | Scientific name | IFO No. or product name |
|---|---|---|
| A-1 | Aspergillus oryzae | Rice koji |
| A-3 | Aspergillus oryzae | Ace Higuchi |
| A-4 | Aspergillus oryzae | BF No. 1 Aspergillus |
| A-5 | Aspergillus oryzae | W-20 |
| A-6 | Aspergillus oryzae | Three Diamonds |
| A-7 | Aspergillus sojae | Soja No. 12 |
| A-8 | Aspergillus kawachi | Honkakushochu-kin for rice |
| A-9 | Monascus pilosus | IFO No. 4520 |
| A-14 | Monascus pubigerus | IFO No. 4521 |
| A-24 | Monascus ruber | IFO No. 9203 |
| A-25 | Monascus vitreus | IFO No. 7537 |
| A-26 | Monascus pilosus | IFO No. 4480 |

Example 1

Production of Fermented Garlic Compositions, and Anti-Oxidation Activity Thereof (Preparation of Fermented Compositions (Extracts))

Garlic was washed with water, and boiled with an equal volume of water for 30 minutes. The garlic was crushed, to thereby obtain a juice. Water in an equal volume and glucose (2%) were added to the mixture. The mixture was subjected to sterilization in an autoclave at 121° C. for 20 minutes (garlic culture medium). Separately, Aspergillus oryzae was pre-cultured by use of Sabouraud's medium (peptone 1%, glucose 4%) under the conditions of 27° C. and 160 rpm shaking for 3 days. The pre-cultured mixture (1%) was added to the garlic culture medium. The resultant mixture was cultured under the conditions of 27° C. and 160 rpm shaking for 2 days to 5 weeks, and subjected to centrifugation at 300 rpm for 10 minutes, to thereby obtain a supernatant (extract). The supernatant was subjected to the following test. Meanwhile, rice and soybeans were prepared such that in each case the weight of solid thereof was equal to that of the garlic culture medium when dried.

Method for Measuring Superoxide Anion Elimination Activity

Each of the samples obtained above (100 $\mu$l) and xanthine oxidase (200 $\mu$l) were added to a mixture of 65 mM $KH_2PO_4$-borate buffer solution (pH 8.2) (200 $\mu$l), 5 mM aqueous xanthine solution (200 $\mu$l), 10 mM aqueous hydoxylamine solution (100 $\mu$l), and water (200 $\mu$l), and the mixture was incubated at 37° C. for 15 minutes. Upon completion of incubation, 30 $\mu$M N-naphtylethylenediamine-3 mM sulfanilic acid-25% glacial acetic acid (2 ml) was added to the reaction mixture so as to terminate the reaction and develop coloring. The reaction mixture was allowed to stand at room temperature for 45 minutes, and subjected to measurement of absorbance at 550 nm. Measurement was carried out twice, to thereby determine active oxygen elimination activity (%) on the basis of decrease in absorbance induced by addition of the sample. In addition, the amount of xanthine oxidase (xanthine oxidase suspension: product of Wako Pure Chemicals Industries, Ltd.) was adjusted such that the absorbance changed at a rate of 0.020–0.025/minute (15–20 mU/ml).

Figure 2:
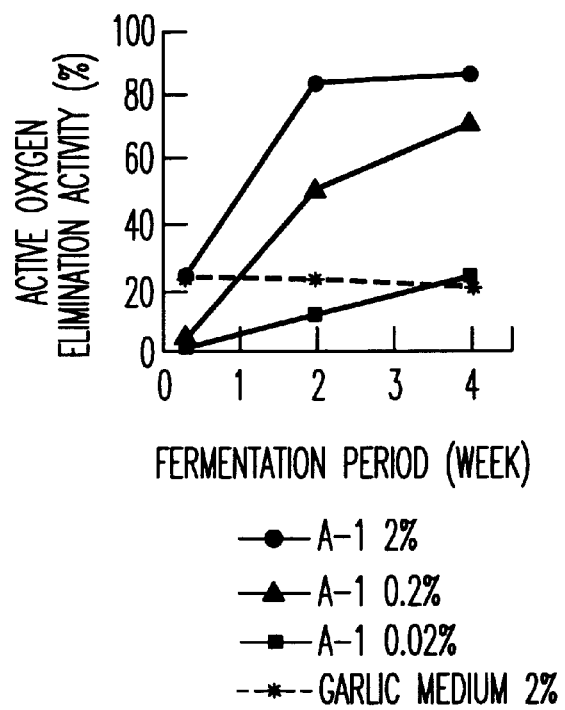
FIG. 2 is a graph showing active oxygen elimination activity.

The results are shown in FIGS. 1 and 2.

Method for Measuring DPPH Radical Elimination Activity

Figure 3:
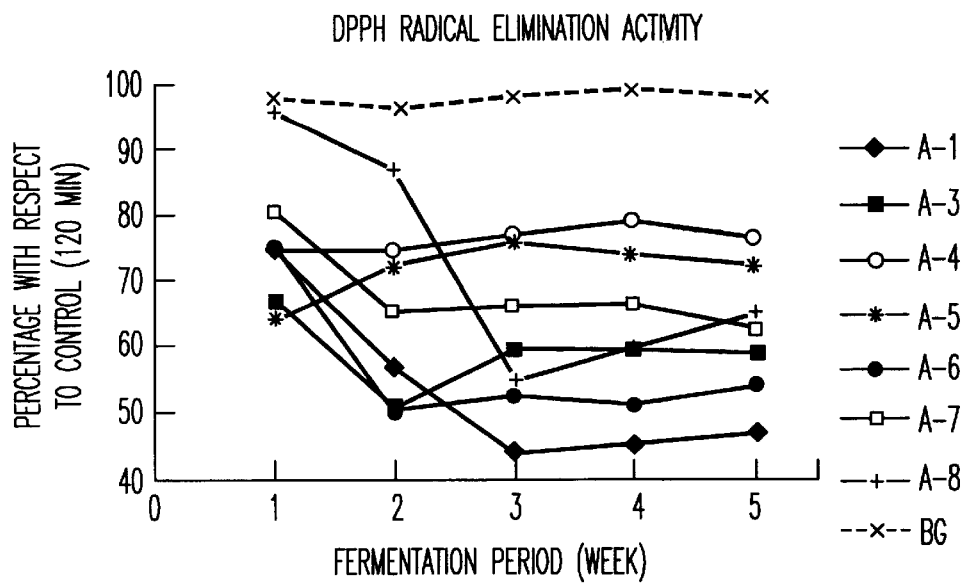
FIGS. 3 through 7 are graphs showing DPPH radical elimination activity.
Figure 4:
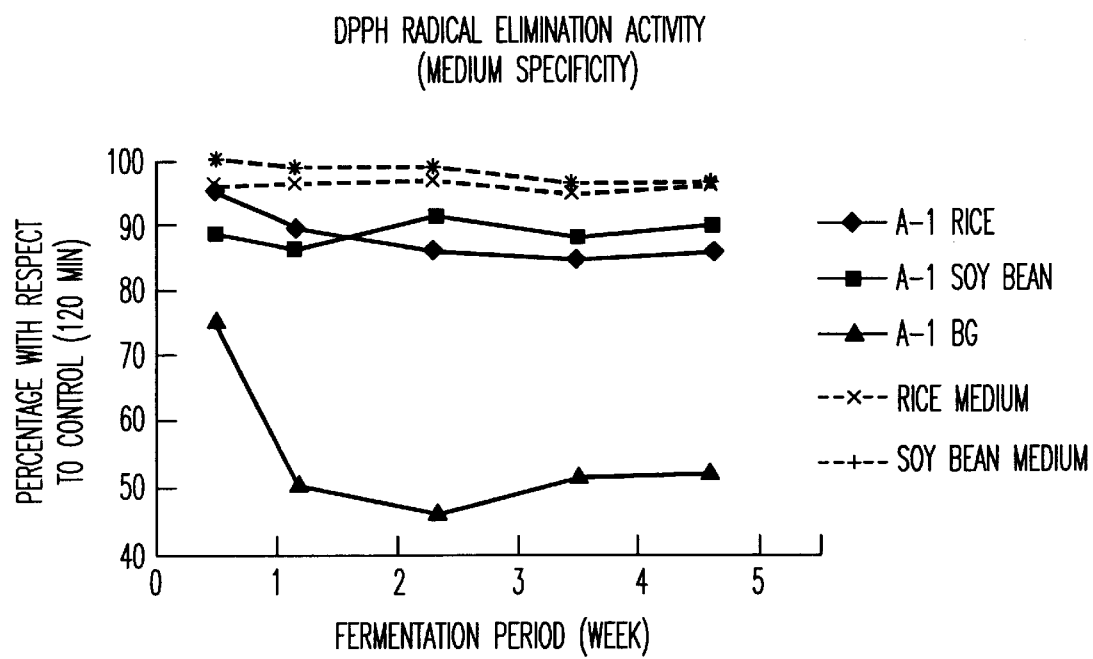
Figure 5:
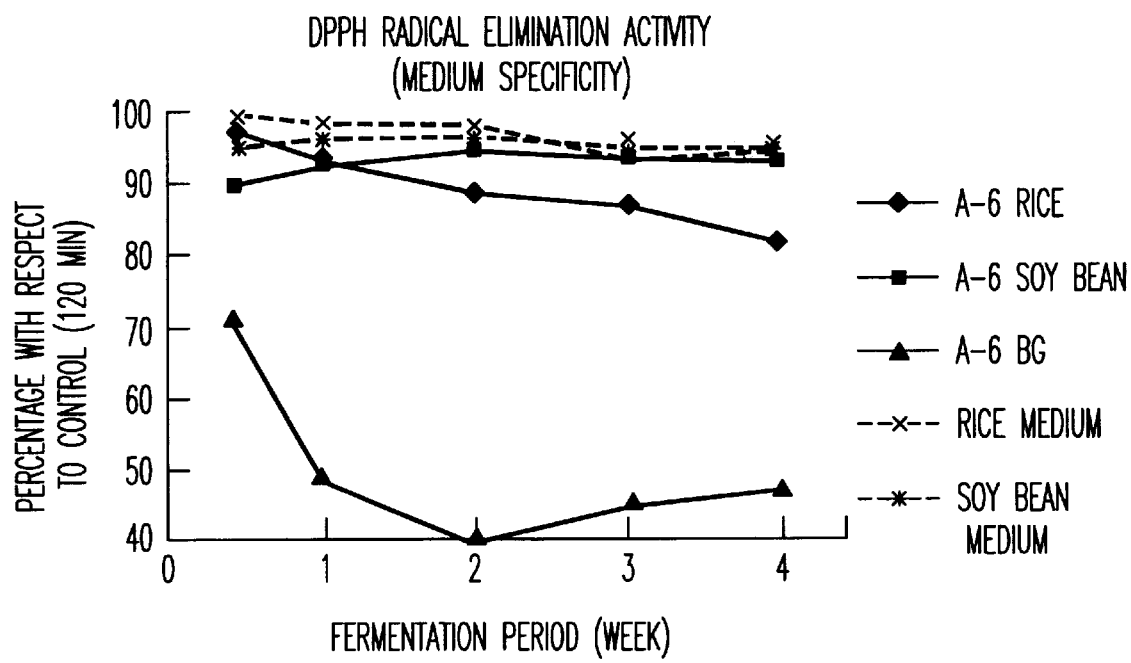

Each of the samples obtained above was diluted with 0.5 M acetate buffer solution (pH 5.5). Ethanol (0.5 ml) was added to the mixture (0.5 ml), and 0.5 mM ethanolic solution of DPPH (1,1-diphenyl-1-2-picrylhydrazyl: product of Wako Pure Chemicals Industries, Ltd.) (0.25 ml) was further added to the mixture. The resultant mixture was mixed well, and subjected to measurement of absorbance at 520 nm over time, to thereby obtain percentage with respect to a control containing no sample. The results are shown in FIGS. 3–5.

Results (1) Superoxide Anion Elimination Activity of the Garlic Culture Medium and the Garlic Fermentation Extract Although the garlic culture medium exhibited weak elimination activity, the garlic fermentation extract exhibited elimination activity that increased with the period of fermentation. Although addition of glucose to the garlic culture medium increased activity of the medium slightly, addition of glucose to the garlic fermentation extract made almost no difference (FIG. 1).

The garlic fermentation extract was diluted, and superoxide anion elimination activity thereof was measured in a manner similar to that described above. A 100-fold diluted sample of the garlic fermentation extract obtained through 4-week fermentation exhibited the same activity as the garlic culture medium. That is, the superoxide anion elimination activity of the garlic extract increased to 100-fold by fermentation (FIG. 2).

(2) DPPH-Radical Elimination Activity

The DPPH-radical elimination activity of 100-fold diluted samples was measured. The garlic culture medium (BG) exhibited almost no activity; however, all of the garlic fermentation extracts which had undergone fermentation by use of any Aspergillus strain exhibited DPPH-radical elimination activity which increased with the period of fermentation. Particularly, samples A-1 and A-6 exhibited high activity (FIG. 3).

(3) Effect of Culture Medium on Production of a Substance Having DPPH-Radical Elimination Activity by use of A-1 and A-6

Rice culture medium and soybean culture medium exhibited almost no DPPH radical elimination activity. The rice culture medium used in combination with A-1 exhibited weak DPPH radical elimination activity, and the soybean culture medium used in combination with of A-1 exhibited even weaker activity. However, when A-1 was used in combination with a fermentation extract obtained by use of garlic culture medium, extremely strong activity was obtained (FIG. 4). Particularly, when A-6 was used, significantly high culture medium specificity was noted with garlic culture medium (FIG. 5).

Example 2

Anti-Oxidative Activity of Garlic Fermentation Extract Obtained by Use of Monascus Preparation of Fermentation Extract Garlic was washed with water, and boiled with an equal volume of water for 30 minutes. The garlic was crushed, to thereby obtain a juice. Water in an equal volume and glucose (2%) were added to the mixture. The mixture was subjected to sterilization in an autoclave at 121° C. for 20 minutes (garlic culture medium). Separately, a platinum loop amount of a Monascus microorganism (the genus Monascus) was cultured by use of a glycerin medium (glycerin 7%, glucose 3%, Soybean meal 3%, peptone 0.8%, magnesium sulfate 0.1%, and sodium chloride 0.2%). The resultant culture liquid (1%) was added to the garlic culture medium. The resultant mixture was cultured under the conditions of 25° C. and 160 rpm shaking for 2–5 weeks, and subjected to centrifugation at 300 rpm for 10 minutes, to thereby obtain a supernatant (extract). The supernatant was subjected to the following test. The test was also carried out on a soybean culture medium prepared such that the weight of soybean was equal to that of the solid of the garlic culture medium when dried, as well as on a culture medium prepared from a mixture of garlic and soybean.

Method for Measuring DPPH Radical Elimination Activity

Figure 6:
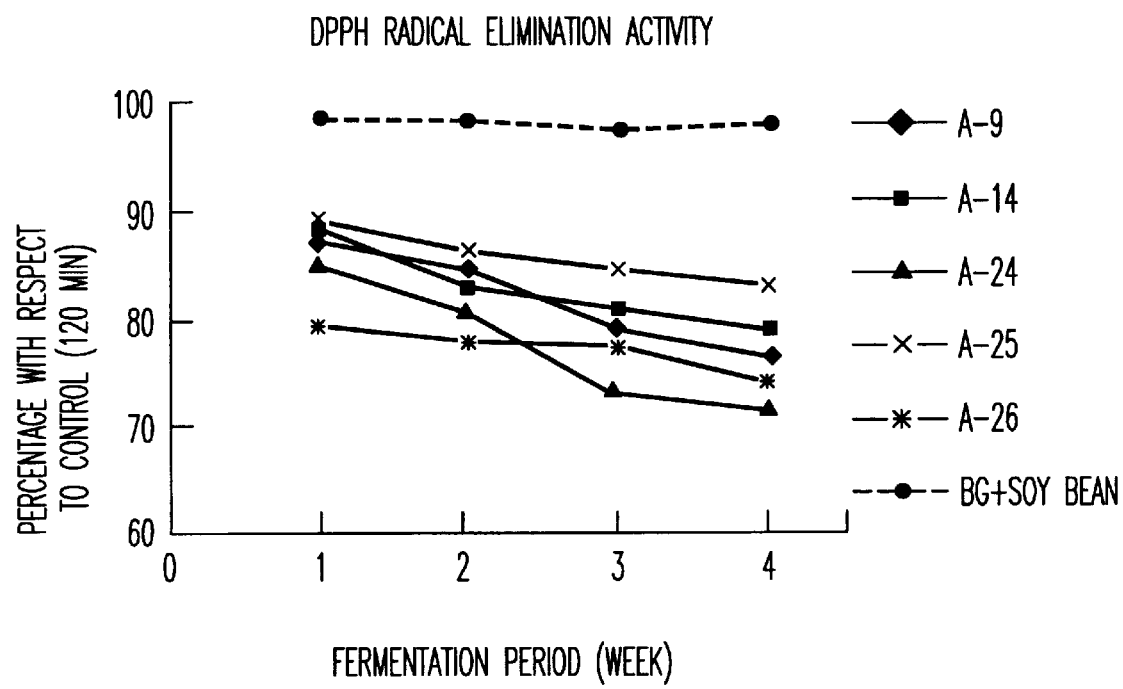
Figure 7:
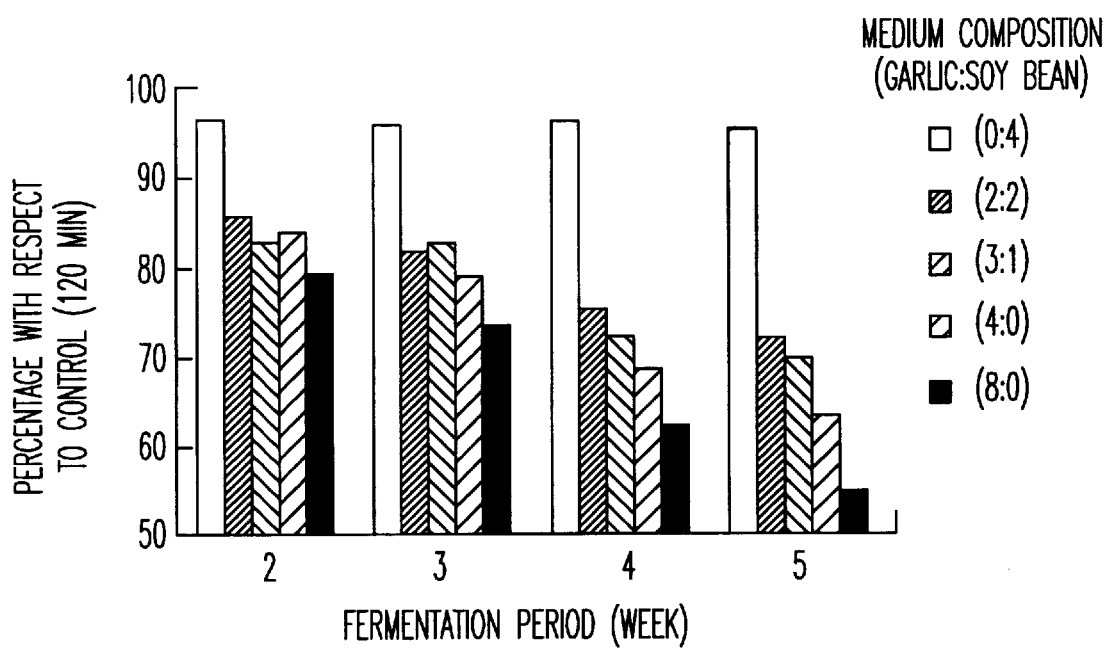

Each of the obtained samples was diluted with 0.5 M acetate buffer solution (pH 5.5). Ethanol (0.5 ml) was added to the mixture (0.5 ml), and 0.5 mM ethanolic solution of DPPH (1,1-diphenyl-1-2-picrylhydrazyl: product of Wako Pure Chemicals Industries, Ltd.) (0.25 ml) was further added to the mixture. The resultant mixture was mixed well, and subjected to measurement of absorbance at 520 nm over time, to thereby determine percentage with respect to a control containing no sample. The results are shown in FIGS. 6–7.

Results (1) DPPH-Radical Elimination Activity of Monascus Culture Mixtures

A culture medium prepared from a mixture of garlic and soybean (the ratio of garlic/soybean: 2/2) exhibited weak elimination activity; however, garlic fermentation extracts which had undergone fermentation by use of Monascus exhibited activity which increased with the period of fermentation. Particularly, A-24 and A-26 exhibited high activity (FIG. 6).

The activity of culture media fermented with A-24 strain was investigated in the case of mixtures having different ratios of garlic to soybean. The culture medium prepared only from soybean (0:4) exhibited weak radical elimination activity; however, the medium prepared from garlic and soybean exhibited activity which increased with the amount of added garlic. Particularly, culture medium prepared from twice the concentration of garlic (8:0) exhibited the highest activity (FIG. 7).

Example 3

Antitumor Effect and Immunity-Enhancing Activity of Fermented Garlic Composition Method for Preparing a Fermented Garlic Composition Garlic was washed with water, and boiled with an equal volume of water for 30 minutes. The garlic was crushed, to thereby obtain a juice. Water in an equal volume and glucose (2%) were added to the mixture. The mixture was subjected to sterilization in an autoclave at 121° C. for 20 minutes (garlic culture medium). Separately, *Aspergillus oryzae* was pre-cultured by use of Sabouraud's medium (peptone 1%, glucose 4%) under the conditions of 27° C. and 160 rpm shaking for 3 days. The pre-cultured mixture (1%) was added to the garlic culture medium. The resultant mixture was cultured under the conditions of 27° C. and 160 rpm shaking for 2 weeks. The obtained fermented product was heated at 100° C. for 10 minutes, freeze-dried, and crushed. When the fermented garlic composition was subjected to a variety of tests, the composition was suspended in water and administered perorally.

Experimental Method

ICR male mice (7 weeks old, purchased from Nihon Crea) were subcutaneously implanted with sarcoma-180 in an amount of $10^6$ cells/mouse. The products to be tested were perorally administered 10 times to each mouse every two days from the day following implantation. The size of a tumor (($\frac{3}{4}$)×minor diameter×minor diameter×major diameter (mm$^3$) on the day following the final administration was measured. Subsequently, the spleen was aseptically removed from each mouse. A cell suspension was prepared by a customary method, treated with Tris buffer for removing erythrocytes (17 mM tris(hydroxymethyl)aminomethane 0.747%, NH$_4$Cl, pH 7.65), washed with RPMI 1640, and suspended in RPMI 1640 containing 10% FCS.

Labeling of YAC-1 Cells and Salcoma 180 Cells

YAC-1 cells or Salcoma 180 cells were added to RPMI 1640 containing 10% FCS, to thereby obtain a cell concentration of 2×10$^6$ cells/0.1 ml. Na$_2$$^{51}$CrO$_4$ (100 μl) (product of Amarsham, 1 μCi/μl in sterile 0.9% NaCl) was added to each of the samples, and both of the samples were cultured in a CO$_2$ incubator for 2 hours. Subsequently, the samples were washed 4 times with RPMI 1640 containing 10% FCS, and adjusted to a concentration of 3×10$^5$ cell/ml.

NK Activity and Killer Activity

Spleen cells were adjusted to a concentration of 3×10$^7$ cell/ml (200 times of YAC-1 cells or Salcoma-180 cells), and 100 μl (3>10$^6$ cells) of the cell suspensions was placed in a NUNC 96-well plate having a U-shaped bottom. $^{51}$Cr-labeled YAC-1 cells adjusted to a concentration of 3×10$^5$ cells/ml or Salcoma-180 cells (50 μl) (1.5×10$^4$ cells) were added thereto (Exp). Further, samples prepared by addition of 1N HCl (100 μl) to $^{51}$Cr-labeled YAC-1 cells or Salcoma-180 cells (50 μl) (1.5×10$^4$ cells) were provided for maximum liberation (Tmax). Samples prepared by addition of RPMI 1640 containing 10% FCS (100 μl) to $^{51}$Cr-labeled YAC-1 cells or Salcoma-180 cells (50 μl) (1.5×10$^4$ cell) were provided for spontaneous liberation (Tspon). The plate having the above-described cells therein was cultured in a CO$_2$ incubator for 24 hours, and centrifuged, to thereby obtain a supernatant. The supernatant (100 μl) was placed in an RIA tube, and subjected to measurement of $^{51}$Cr liberated by use of a gamma counter. Cytotoxicity (%) was calculated from the following equation. The calculated cytotoxicity was regarded as NK activity or killer activity.

$$\text{Cytotoxicity (\%)} = ((\text{Exp}-\text{Tspon})/(\text{Tmax}-\text{Tspon})) \times 100$$

Statistical Processing

Following an F test, a Student's t-test or Aspin-Welch test was performed, wherein the level of significance was set to <5%. Statistically significant data are marked with "*." The results are shown below.

Results (1) Anti-Tumor Effect

In contrast to the tumor volume as measured three weeks after implantation of cancer cells in the control group (393 mm$^3$), the tumor volume of the group administered A-1 and the tumor volume of the group administered A-6 exhibited statistically significant proliferation inhibitory effect. The group administered Krestin exhibited a similar statistically significant proliferation inhibitory effect.

TABLE 2

Tumor volume three weeks after implantation (mm$^3$)

| | Peroral dose | N | Tumor volume (mm$^3$) |
|---|---|---|---|
| Control | Water 10 ml/kg/2 days × 10 | 10 | 393 ± 48 |
| A-1 | 2 g/10 ml/kg/2 days × 10 | 9 | 219 ± 33* |
| A-6 | 2 g/10 ml/kg/2 days × 10 | 9 | 230 ± 35* |
| Krestin | 1 g/10 ml/kg/2 days × 10 | 10 | 164 ± 30* |

(2) NK Activity

Spleen cells obtained from mice three weeks after implantation with cancer cells were used to measure NK activity. The NK activity in the control group was 4.6%, whereas that in the group administered A-1 was 17.8% and that in the group administered A-6 was 14.1%, showing statistically significant NK activity enhancement action. The group administered Krestin exhibited a similar statistically significant proliferation inhibitory effect.

TABLE 3

NK activity
(against YAC-1 cells, cytotoxicity (%))

|  | N | Mean ± SE |
|---|---|---|
| Normal | 2 | 1.0 ± 0.9 |
| Control | 10 | 4.6 ± 1.7 |
| A-1 | 9 | 17.8 ± 5.5* |
| A-6 | 9 | 14.1 ± 3.1* |
| Krestin | 10 | 10.5 ± 3.5* |

(3) Killer Activity

Spleen cells obtained from mice three weeks after implantation with cancer cells were used to measure killer activity. As in the case of NK activity, the killer activity in the group administered A-1 and that in the group administered A-6 were remarkable and showed statistically significant activity enhancement effect.

TABLE 4

Killer activity
(against S180 cells, cytotoxicity (%))

|  | N | Mean ± SE |
|---|---|---|
| Normal | 2 | 8.4 ± 6.7 |
| Control | 10 | 0.2 ± 2.2 |
| A-1 | 9 | 19.8 ± 5.8* |
| A-6 | 9 | 20.1 ± 3.2* |
| Krestin | 10 | 2.2 ± 1.6 |

Example 4

Activity for Protection from Acetoaminophene Liver Disorder

Experimental Method

The same fermented garlic composition as in Example 3 was employed. 6-week-old ddY male mice (Japan SLC) were provided and each mouse was made to fast overnight. The test substance was orally administrated to each mouse twice; e.g., 2 hours after and 30 minutes before the administration of acetoaminophene (400 mg/kg) in the abdominal cavity. After 6 hours, blood was collected through the abdominal aorta by use of a heparin-treated syringe, after which GPT activity in plasma was measured as an index of liver disorder. Acetoaminophene (product of Wako Pure Chemicals Industries, Ltd.) was dissolved in a physiological saline solution which had been adjusted to pH 11 with an aqueous potassium phosphate solution (100 mg/ml) in a boiling water bath. GPT activity in plasma was measured by use of "GPT-UV TEST WAKO" (product of Wako Pure Chemicals Industries, Ltd.). The results are shown below.

Results

The administration of acetoaminophene increased plasma GPT activity of the control group up to 468 IU/l and induced a severe liver disorder. In contrast, plasma GPT activity of the group to which A-1 had been administered increased to 146 IU/l and GPT activity in plasma of the group to which A-6 had been administered increased to 68 IU/l and therefore significant activity for protection against liver disorder was observed.

TABLE 5

Protection against acetoaminophene liver disorder

|  | Peroral dose | Acetaminophene | N | Plasma GPT activity (IU/1) |
|---|---|---|---|---|
| Normal | Water 10 ml/kg × 2 | — | 5 | 4 ± 0.3 |
| Control | Water 10 ml/kg × 2 | 400 mg/kg i.p. | 10 | 468 ± 112 |
| A-1 | 2 g/10 ml/kg × 2 | 400 mg/kg i.p. | 9 | 146 ± 87* |
| A-6 | 2 g/10 ml/kg × 2 | 400 mg/kg i.p. | 9 | 68 ± 51* |

(*:p < 0.01 by Kruskal-Wallis test)

Example 5

Anti-Diabetes Activity

Experimental Method

The same fermented garlic composition as in Example 3 was employed. 6-week-old ddY male mice (Japan SLC) were provided and each mouse was made to fast overnight. 20 µl of blood was taken from the orbital venous plexus of the mouse by use of a capillary. A test substance (4 g/kg) was administered orally to each mouse, and after elapse of one hour, 50 mg/kg of alloxan (product of Wako Pure Chemicals Industries, Ltd.) was administered intravenously, and blood was collected in the same manner after elapse of 1 hour and 6 hours. The mice were fed immediately after the administration of alloxan, and the test substance was orally administrated once daily from one day before to three days following administration of alloxan. Blood was collected in the same manner 1, 2, and 4 days thereafter. Immediately after the blood collection, plasma was separated by use of a hematocrit centrifuge, after which blood sugar value was measured by use of "Glucose CII—Test Wako" (product of Wako Pure Chemicals Industries, Ltd.).

Figure 8:
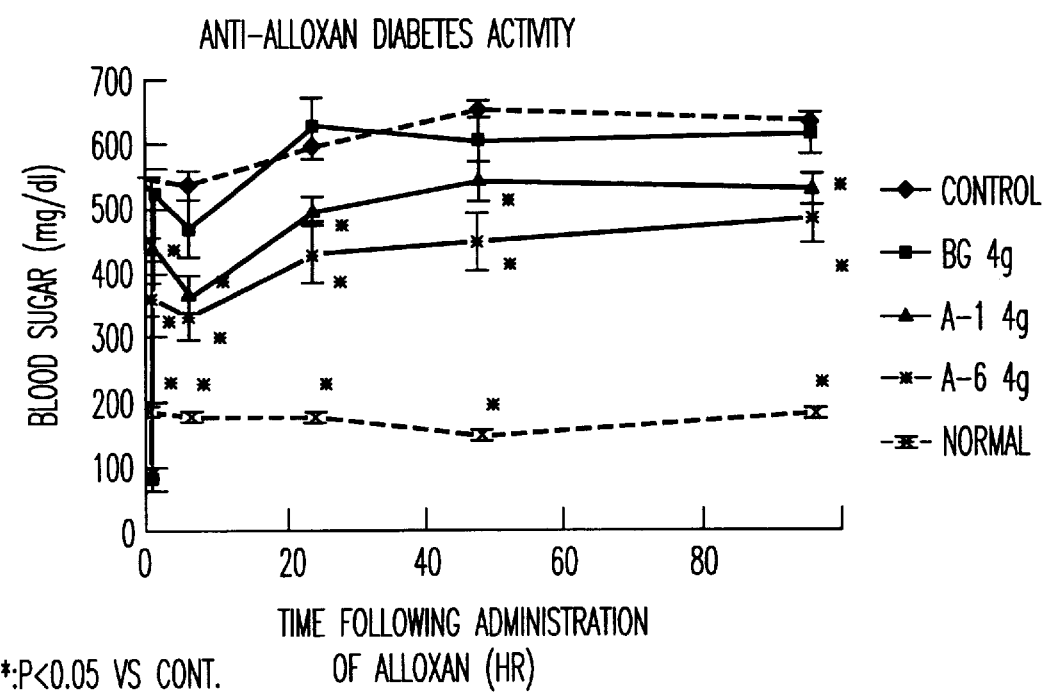
FIG. 8 is a graph showing activity for inhibiting alloxan diabetes.

The results of measurement were statistically processed as in Example 3. The results are shown in FIG. 8.

TABLE 6

Test using an alloxan diabetes model

| Test group | N | Oral administration of a test substance | Alloxan |
|---|---|---|---|
| Normal | 5 | Water 20 ml/kg/day × 5 | — |
| Control | 10 | Water 20 ml/kg/day × 5 | 50 mg/kg i.v. |
| Boiled garlic | 10 | 4 g/20 ml/kg/day × 5 | 50 mg/kg i.v. |
| A-1 | 10 | 4 g/20 ml/kg/day × 5 | 50 mg/kg i.v. |
| A-6 | 10 | 4 g/20 ml/kg/day × 5 | 50 mg/kg i.v. |

Results

The blood sugar value of mice in a normal state, shown as "normal" in the Table, was about 200 mg/dl. In contrast, after administration of alloxan, the blood sugar value of the control group increased to 540 mg/dl after elapse of one hour and the value continued to increase thereafter, to 650 mg/dl after elapse of 48 hours. In contrast, after elapse of one hour from the administration of alloxan, the blood sugar value of the group to which the fermented garlic composition A-6 had been administered remained at 380 mg/dl. Accordingly, there was observed a statistically significant activity for inhibiting the increase of blood sugar as compared with the control group. Even thereafter, a statistically significant low value was obtained. A-1 also showed significant activity for inhibiting increase in blood sugar level. In contrast, when boiled garlic (garlic culture medium: BG) used as the material for fermentation was administered, the increase in blood sugar level caused by alloxan (FIG. 8) was not inhibited.

Example 6

Activity for Inhibiting Increase of Blood Sugar

Experimental Method

The same fermented garlic composition as in Example 3 was employed. 8-week-old ddY male mice (Japan SLC) were provided and each mouse was made to fast overnight. Subsequently, 20 μl of blood was taken from the orbital venous plexus by use of a capillary and no water was given until the end of the experiment. The test substance and starch were simultaneously orally administered to each mouse and blood was collected in the same manner after elapse of 30, 60, and 120 minutes. Immediately after blood collection, plasma was separated by use of a hematocrit centrifuge, followed by the measurement of a blood sugar value using "Glucose CII—Test Wako" (product of Wako Pure Chemicals Industries, Ltd.).

Figure 9:
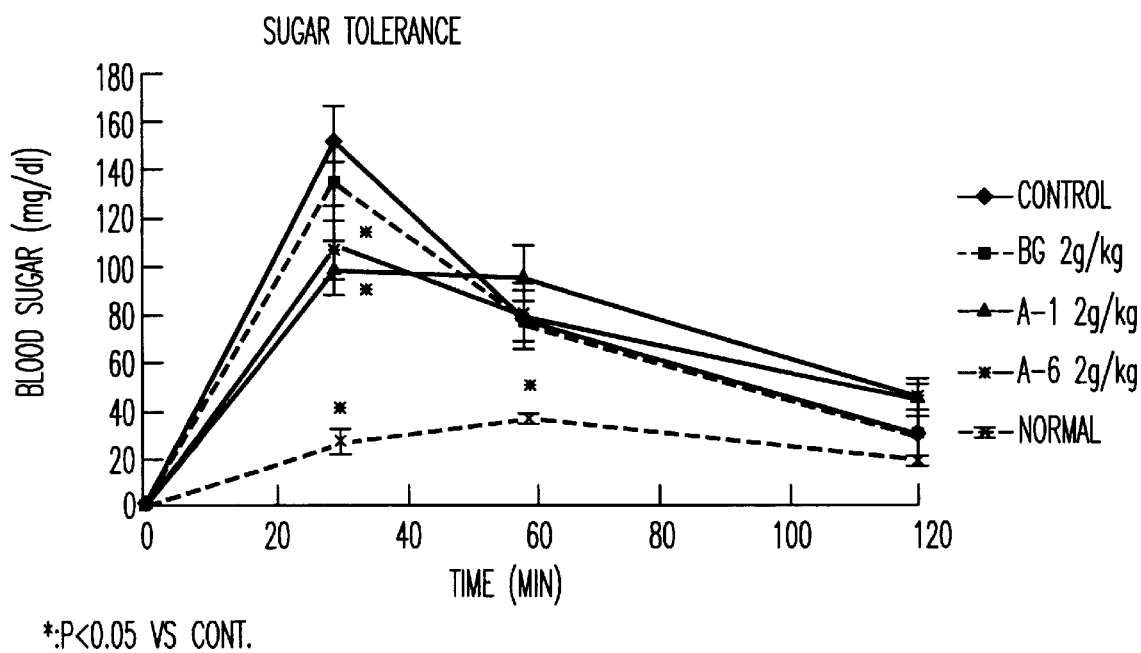
FIG. 9 is a graph showing glucose tolerance.

The results of measurement were subjected to the same statistical processing as in Example 3. The results are shown in FIG. 9.

TABLE 7

| | | Glucose tolerance test | |
|---|---|---|---|
| Test group | N | Test substance | Starch |
| Normal | 10 | Water 10 ml/kg | Water 10 ml/kg |
| Control | 8 | Water 10 ml/kg | 1 g/10 ml/kg |
| Boiled garlic | 8 | 2 g/10 ml/kg | 1 g/10 ml/kg |
| A-1 | 8 | 2 g/10 ml/kg | 1 g/10 ml/kg |
| A-6 | 8 | 2 g/10 ml/kg | 1 g/10 ml/kg |

Results

In a control group to which starch was administered orally, blood sugar level increased to 150 mg/dl by the end of 30 minutes. In contrast, in the group administered A-1, increase in blood sugar level was only 100 mg/dl, showing statistically significant activity of A-1 for inhibiting the increase of blood sugar with respect to the control group. Thereafter, without statistical significance, the blood sugar level varied within a range slightly higher than that as observed in the control group, and a delayed increase in blood sugar level was observed. In the group administered A-6, results almost identical with those for the group administered A-1 were obtained. In contrast, in groups administered boiled garlic (garlic culture medium: BG), the increase in blood sugar level followed a course similar to that observed in the control group, providing results which were clearly different from those for the fermented garlic composition (FIG. 9).

Example 7

Inhibitory Activity of Garlic Fermentation Extract Obtained by use of Monascus Against Cholesterol Synthesis The same garlic fermentation extract as in Example 2 was employed.

Method for Preparing Enzyme Samples

Wistar male rats (6.5 weeks old) were fed powdery EC-2 (product of Nihon Crea) and acclimated for six days under night-and-day reversed lighting (lighting time: 17:00–05:00). Subsequently, the rats were fed for 5 days with CE-2 mixed with 2% cholestiramin and 8% corn oil. At 10:00, which corresponded to late night, the rats were sacrificed by exsanguination for removal of the liver. Phosphate buffer was added to the liver in a volume twice that of the liver while cooling on ice, and then homogenized with a Teflon homogenizer. Thereafter, a microsome fraction was obtained as described below, and the protein content was adjusted to 10 mg/ml. The thus-prepared sample was stored at −80° C.

Rat liver homogenate
  ↓ Centrifugal separation (700 g, 5 min)
Supernatant
  ↓ Centrifugal separation (12,000 g, 30 min)
Supernatant
  ↓ Centrifugal separation (105,000 g, 60 min)
Sediment (washing)
  ↓ Centrifugal separation (105,000 g, 60 min)
Sediment (microsome fraction)
  ↓ Suspension in phosphate buffer
    (protein content 10 mg/ml)

Method for Measuring HMG-CoA Reductase Inhibitory Activity

An enzyme solution for reaction (50 μl) was prepared so as to contain the reagents listed below, and subjected to reaction at 37° C. for 30 minutes. Reaction was induced by the addition of the enzyme solution, and stopped by the addition of 2N HCl (20 μl). After addition of HCl incubation was performed at 37° C. for 15 minutes. Subsequently, 450 μl of a cation exchange resin (bio rex 5, product of BioRad) suspension (1 g/10 ml) was added thereto, and the resultant mixture was shaken for one hour. The supernatant (400 μl) was added to 10 ml of a liquid scintillator (ACS II, product of Amersham), and $^{14}C$ released from CoA was counted.

The amount of the test substance (i.e., a fermentation extract obtained from the method described in Example 2) contained in the enzyme solution for reaction (50 μl) was 10 μl. $IC_{50}$ value was calculated through a Litchfield-Wilcoxon method by use of the data as obtained at three or more points which encompass 50% inhibition.

Composition of the enzyme solution for reaction:
  0.11 mM dl[3-$^{14}C$]HMG-CoA (2.25 Ci/mol)
  100 mM potassium phosphate buffer
  10 mM EDTA
  10 mM dithiothreitol
  5 mM NADPH
  30–40 μg microsomal protein (in 50 μl of the solution for reaction)

Results

Figure 10:
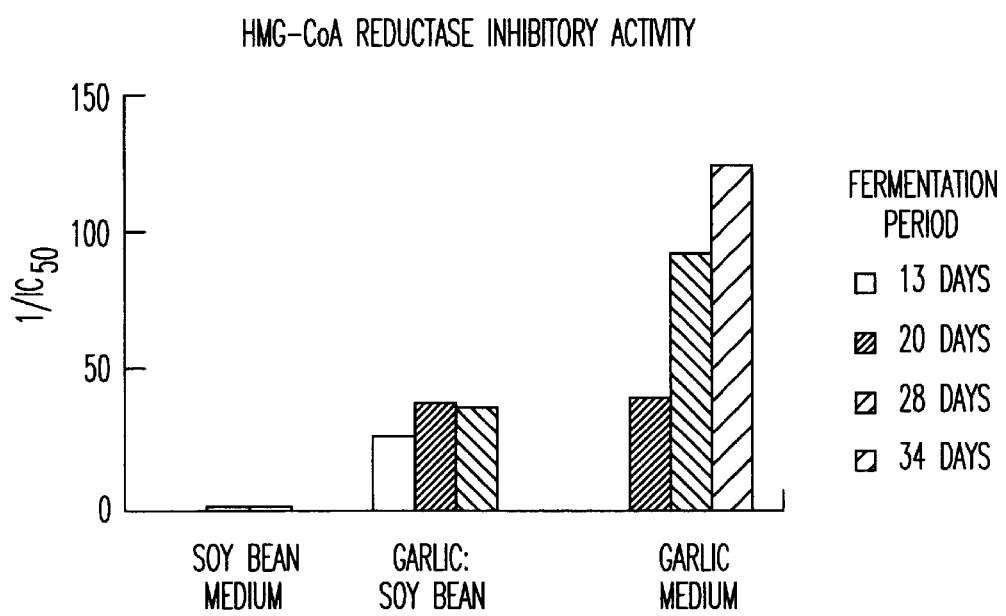
FIG. 10 is a graph showing activity for inhibiting HMG-CoA reductase.

FIG. 10 shows the HMG-CoA reductase inhibitory activity (shown by the inverse of $IC_{50}$) of each of culture liquids, which were prepared by adding a Monascus microorganism (strain A-24) to a soybean medium, a mixed medium of garlic and soybean (1:1), or a garlic medium, and incubating for 13–34 days. In the case of the soybean medium, almost no inhibitory activity was observed throughout the test period. In contrast, in the case of the mixed medium of garlic and soybean, an inhibitory activity of 0.03–0.02 ml/ml $IC_{50}$ was observed. In the garlic medium, strong inhibitory activity was observed in accordance with the culture period ($IC_{50}$ value: 0.02–0.007 ml/ml) (FIG. 10).

These results confirm that enzymatically-deactivated garlic, when used in combination with a Monascus microorganism, effectively produces a substance having HMG-CoA reductase inhibitory activity.

Example 8

Formulation Example—Tablets

To the fermented garlic composition prepared in Example 3 were added lactose, corn starch, crystalline cellulose, carmellose-Ca, sodium alginate, agar powder, sodium hydrogencarbonate, and magnesium stearate in amounts shown below. The ingredients were mixed for 10 minutes by use of a Boray container mixer (manufactured by Kotobuki Giken Kogyo K.K.). The powdery mixture was compression-molded with a tableting machine (clean press correct 19K, manufactured by Kikusui Seisakusho), to thereby obtain tablets each having a diameter of 8 mm and weighing 180 mg. The tablets exhibited excellent hardness and disintegration in the stomach.

TABLE 8

Formulation of tablets

| Ingredient | Weight (%) |
|---|---|
| Fermented garlic composition | 50 |
| Corn starch | 25 |
| Crystalline cellulose | 14 |
| Carmellose-Ca | 10 |
| Magnesium stearate | 1 |
| Total | 100 |

Example 9

Formulation Example—Granules

To the fermented garlic composition prepared in Example 3 were added corn starch, crystalline cellulose, hydroxypropylcellulose, and carmellose-Ca in amounts shown below, and the resultant mixture was kneaded with the addition of water. The kneaded mixture was extruded from a granulating machine (DOME GRAN, manufactured by Fuji Powdal), to thereby yield columnar granules each having a diameter of 0.8 mm. The granules were subjected to particle size regulation, drying, and sieving, to thereby obtain a granule product. This product exhibited excellent gastric disintegration and can be provided in the form of, for example, a portion package.

TABLE 9

Formulation of granules

| Ingredient | Weight (%) |
|---|---|
| Fermented garlic composition | 20 |
| Corn starch | 40 |
| Crystalline cellulose | 25 |
| Hydroxypropylcellulose | 5 |
| Carmellose-Ca | 10 |
| Total | 100 |

Example 10

Formulation Example—Beverage-Type Solution

To the fermented garlic composition prepared in Example 2 were added a sweetener, an acidity-imparting agent, a flavoring agent, and water. The mixture was sterilized and charged in a glass vial, to thereby prepare a beverage-type solution.

TABLE 10

Formulation of beverage-type solution

| Ingredient | Volume |
|---|---|
| Fermented garlic composition | 100 ml |
| Sweetener | Suitable amount |
| Acidity-imparting agent | Suitable amount |
| Flavoring agent | Suitable amount |
| Water | Suitable amount |
| Total | 1000 ml |

INDUSTRIAL APPLICABILITY

The composition of the present invention has no unpleasant odor and is advantageously used as a preventive and therapeutic agent for diseases such as diabetes, hepatic diseases, cancer, immunopathy, and hyperlipemia.

What is claimed is:

1. A composition prepared by fermenting enzymatically-deactivated garlic by the use of Monascus.

2. A composition prepared by adding soybeans and/or cereal to enzymatically-deactivated garlic, followed by fermentation with Monascus.

3. A food containing the composition as recited in claim 1 or 2.

4. A drug containing the composition as recited in claim 1 or 2.

5. A drug according to claim 4 which is for the prevention and treatment of a disease selected from the group consisting of diabetes, hepatic diseases, cancer, immunopathy, and hyperlipemia.

6. A pharmaceutical composition containing a composition as described in claim 1 or 2 and a pharmaceutically acceptable carrier.

7. A method of treating a disease selected from the group consisting of diabetes, hepatic diseases, cancer, immunopathy, and hyperlipemia, comprising administering an effective amount of a composition as described in claim 1 or 2.

8. A process for producing a fermented garlic composition comprising fermenting enzymatically-deactivated garlic by use of Monascus.

9. A process for producing a fermented garlic composition comprising adding soybeans and/or cereal to enzymatically-deactivated garlic, followed by fermentation with Monascus.

10. A composition prepared by:

fermenting enzymatically-deactivated garlic using Aspergillus, or by fermenting soybeans and/or cereal and enzymatically-deactivated garlic using Aspergillus.

11. A method for treatment of a disease selected from the group consisting of diabetes, hepatic diseases, cancer, immunopathy, and hyperlipemia, comprising administering an effective amount of a composition of claim 10.

12. A method of enhancing immunity, providing antioxidative activity and/or providing carcinostatic activity comprising administration of a composition of any one of claims 1, 2 or 10.

13. A method of treatment comprising the administration of a composition as described in claim 1 or 2.

14. A method according to claim 13, wherein said composition is administered to a subject having a disease selected from the group consisting of diabetes, hepatic diseases, cancer, immunopathy, and hyperlipemia.

15. A method of preparing a composition comprising fermenting enzymatically-deactivated garlic or a mixture of soybeans and/or cereal and enzymatically-deactivated garlic using Aspergillus.

* * * * *